United States Patent [19]
Shonk

[11] Patent Number: 5,342,305
[45] Date of Patent: Aug. 30, 1994

[54] VARIABLE DISTENTION ANGIOPLASTY BALLOON ASSEMBLY

[75] Inventor: Robert S. Shonk, Davie, Fla.

[73] Assignee: Cordis Corporation, Miami Lakes, Fla.

[21] Appl. No.: 929,671

[22] Filed: Aug. 13, 1992

[51] Int. Cl.$^5$ .............................................. A61M 29/02
[52] U.S. Cl. .................... 604/101; 606/194
[58] Field of Search ................. 604/96–103; 606/192–196

[56] References Cited

U.S. PATENT DOCUMENTS

| | | | |
|---|---|---|---|
| 3,045,677 | 7/1962 | Wallace | 604/101 |
| 4,327,736 | 5/1982 | Inoue | 604/101 |
| 4,338,942 | 7/1982 | Fogarty | 606/194 |
| 4,608,984 | 9/1986 | Fogarty | 606/194 |
| 4,744,366 | 5/1988 | Jang | 606/194 |
| 4,932,958 | 6/1990 | Reddy et al. | 606/192 |
| 4,983,167 | 1/1991 | Sahota | 606/194 |
| 4,994,033 | 2/1991 | Shockey et al. | 604/101 |
| 5,108,415 | 4/1992 | Pinchuk et al. | 606/194 |

FOREIGN PATENT DOCUMENTS 9211895 7/1992 PCT Int'l Appl. ................ 604/101

OTHER PUBLICATIONS

Beer, F. P., et al., *Mechanics of Materials*, pp. 38–41 (McGraw-Hill 1981).

*Primary Examiner*—John D. Yasko
*Assistant Examiner*—Adam J. Cermak
*Attorney, Agent, or Firm*—Thomas R. Vigil

[57] ABSTRACT

The variable distention angioplasty balloon assembly, for insertion into a blood vessel, comprises an inner elongated, inflatable balloon having a distal portion, a proximal portion and an intermediate portion therebetween and defining therein a first chamber. The inner balloon has a first Young's modulus. The outer elongated, inflatable balloon has a distal portion, a proximal portion and an intermediate portion therebetween positioned around the inner balloon and defines between the balloons a second chamber. The outer balloon has a second Young's modulus. The inner balloon is substantially enclosed by the outer balloon, and the first Young's modulus of the inner balloon is less than the second Young's modulus of the outer balloon. The first chamber of the inner balloon and the second chamber of the outer balloon define a variable dilation structure for dilating an anatomical stricture. The dilation structure with variable characteristics has a first diameter and pressure characteristic curve defined by a first rate of radial expansion dependent on the Young's modulus of the inner balloon and a second diameter and pressure characteristic curve defined a second rate of radial expansion dependent upon the combined Young's modulus of the inner balloon and the outer balloon.

17 Claims, 2 Drawing Sheets

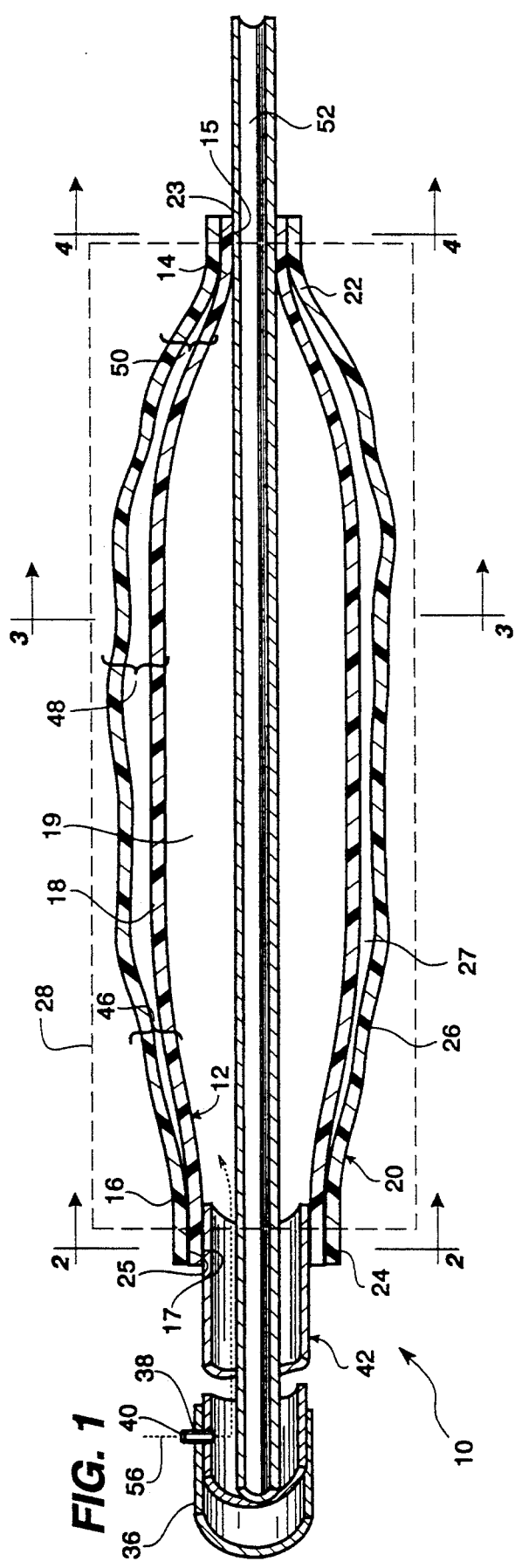
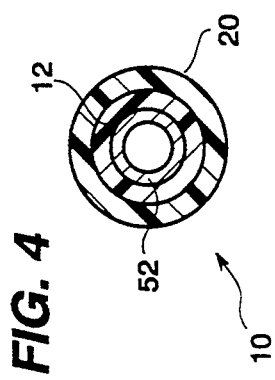
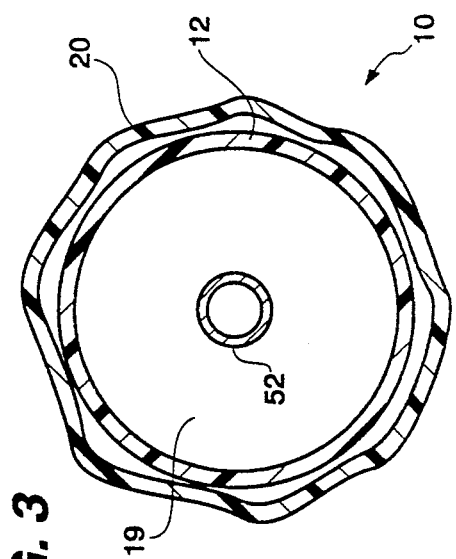
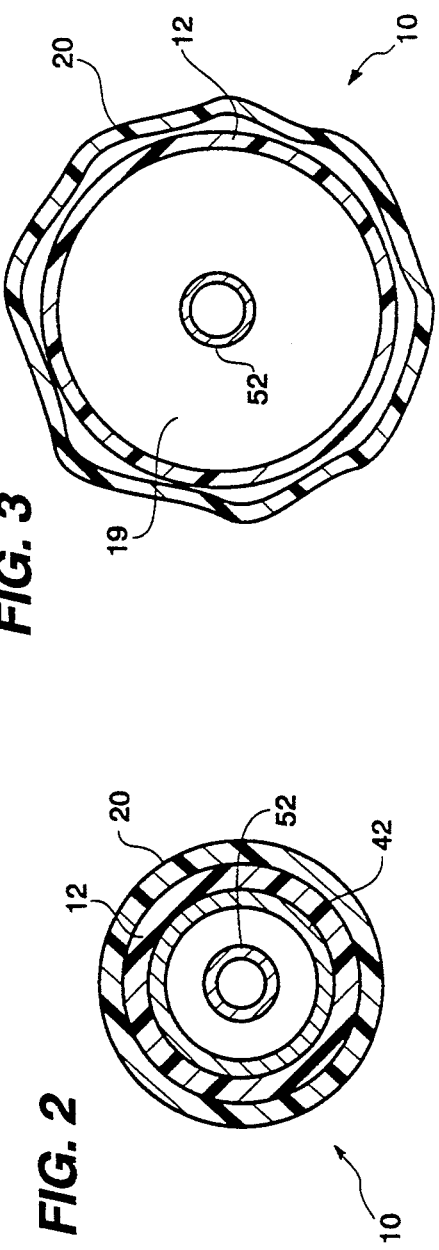

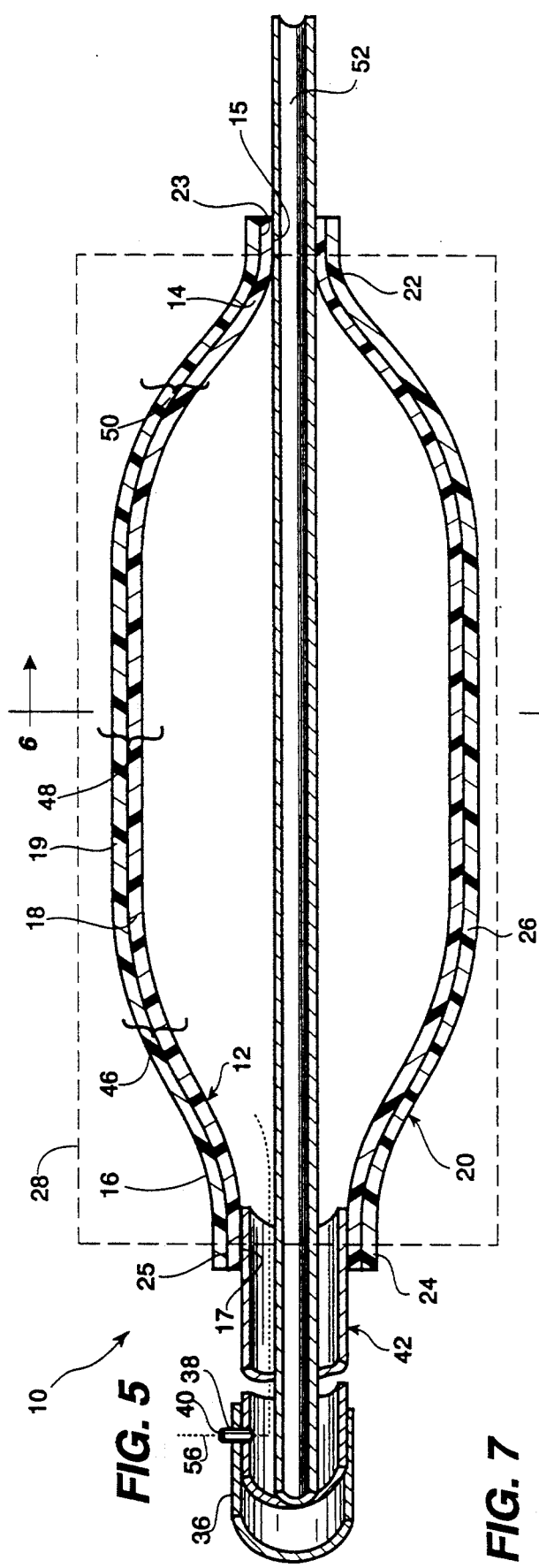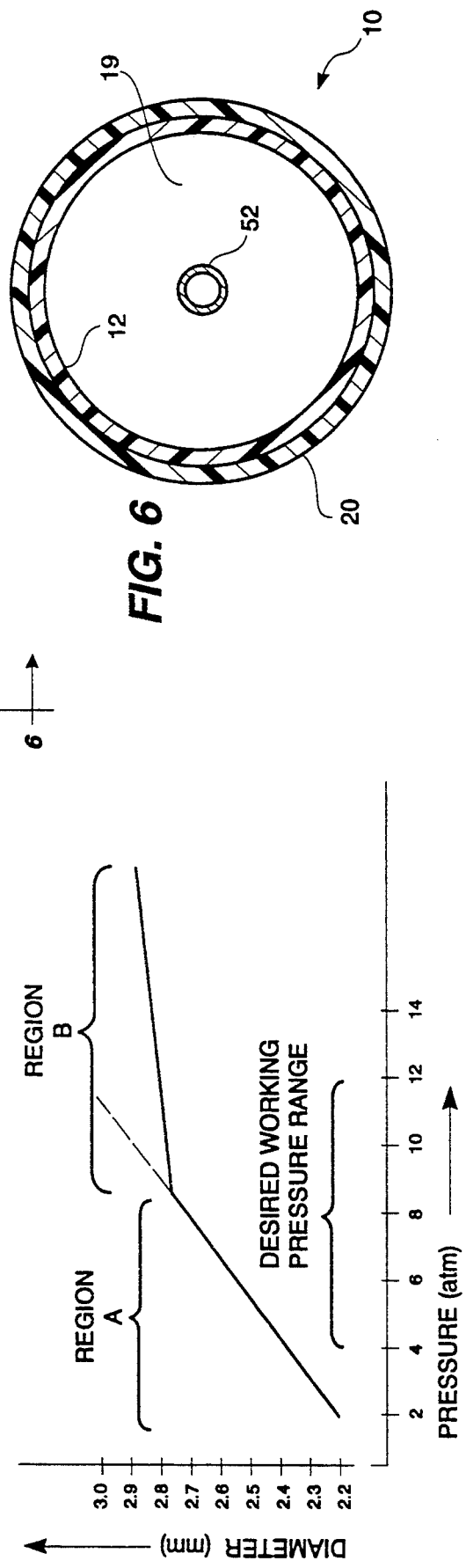

VARIABLE DISTENTION ANGIOPLASTY BALLOON ASSEMBLY

BACKGROUND OF THE INVENTION

1. Field of the Invention

This invention relates to a dilatation balloon assembly and particularly to a novel improvement in variable distention angioplasty balloon assembly.

2. Description of the related art including information disclosed under 37 CFR §§1.97-1.99

Heretofore various angioplasty balloon assemblies have been proposed. Examples of such assemblies are disclosed in the following U.S. Pat. Nos.:

| U.S. Pat. No. | Patentee |
| --- | --- |
| 3,045,677 | F. J. Wallace |
| 4,994,033 | Shockey, et al. |

The Wallace U.S. Pat. No. 3,045,677, discloses a balloon catheter adapted for insertion into a body cavity, such as a bladder, that includes two balloon portions integral with a catheter and having a tube extending over the balloon portions and cemented at opposite ends and to a shaft of the catheter.

The Shockey et al U.S. Pat. No. 4,994,033, discloses an intravascular drug delivery dilatation catheter including an inner expander member having micropores therethrough and an outer expander member also having micropores therethrough.

SUMMARY OF THE INVENTION

According to the present invention there is provided a variable distention angioplasty balloon assembly, for insertion into a blood vessel, comprising: an inner elongated, inflatable balloon having a distal portion, a proximal portion and an intermediate portion therebetween and defining therein a first chamber, in the inner balloon having a first Young's modulus; an outer elongated, inflatable balloon having a distal portion, a proximal portion and an intermediate portion therebetween positioned around the inner balloon and defining between the balloons an evacuated space, the outer balloon having a second Young's modulus, the inner balloon being substantially enclosed by the outer balloon, and the first Young's modulus of the inner balloon is less than the second Young's modulus of the outer balloon; and the first chamber of the inner balloon and the evacuated space of the outer balloon define a variable dilation structure for dilating an anatomical stricture, the dilation structure with variable characteristics having a first diameter and pressure characteristic curve defined by the Young's modulus of the inner balloon and a second diameter and pressure characteristic curve defined by the combined Young's modulus of the inner and the outer balloons.

BRIEF DESCRIPTION OF THE DRAWINGS

FIG. 1 of the drawings is an axial longitudinal sectional view of a variable distention angioplasty balloon assembly in a partially dilated condition, with a catheter aligned and enclosed therein.

FIG. 2 of the drawings is a diametrical sectional view through the assembly in FIG. 1 and is taken along line 2—2 of FIG. 1.

FIG. 3 of the drawings is a diametrical sectional view through the assembly in FIG. 1 and is taken along line 3—3 of FIG. 1.

FIG. 4 of the drawings is a diametrical sectional view through the assembly in FIG. 1 and is taken along line 4—4 of FIG. 1.

FIG. 5 of the drawings is an axial longitudinal sectional view, similar to the view in FIG. 1, illustrating the balloon assembly thereof in a fully expanded condition, with a catheter aligned therein.

FIG. 6 of the drawings is a diametrical sectional view of FIG. 5 and is taken along the line 6—6 in FIG. 5.

FIG. 7 of the drawings is a graph illustrating the predicted pressure and diameter characteristic curve of the balloon assembly in FIG. 1.

DESCRIPTION OF THE PREFERRED EMBODIMENT(S)

Referring now to the drawings in greater detail, illustrated in FIG. 1 is a variable distention angioplasty balloon assembly 10, for insertion into and dilation of an anatomical stricture in a blood vessel or other body cavity.

The multi-layer balloon assembly 10 includes an inner elongated, inflatable balloon 12 having a distal portion 14, a proximal portion 16 and an intermediate portion 18 therebetween and defining therein a first chamber 19. The inner balloon 12 has a pre-selected first Young's modulus thereby having a predicted fixed-linear pressure-diameter characteristic or relationship as illustrated in Region A in FIG. 7.

The assembly 10 further includes an outer elongated, inflatable balloon 20 having a distal portion 22, a proximal portion 24 and an intermediate portion 26 therebetween positioned around the first balloon 20 and defining a second chamber between the balloons. The outer balloon 20 has a second Young's modulus different from the inner balloon 12. The inner balloon 12 is substantially enclosed by and longitudinally coextensive with the outer balloon 20.

In one embodiment, the balloons 12 and 20 are substantially impermeate thereby having the predicted characteristics illustrated in FIG. 7. In one preferred embodiment, the inner and outer balloons 12 and 20 distal portions 14 and 22 include port sections 15 and 23 and the proximal portions 16 and 24 include port sections 17 and 25, respectively, for allowing a catheter and further means for dilating the assembly 10.

In one embodiment, the distal port sections 15 and 23 are adhesively sealed or preferably heat sealed to each other, for a good seal and are attached to a catheter. Also, the proximal port sections 17 and 25 are adhesively sealed or preferably heat sealed to each other for improved seals, and attached to other means, such as a hub or an intermediate section for inflating or dilating assembly 10.

The first chamber 19 of the inner balloon 12 and the second chamber 27 of the outer balloon 20 define a variable dilation structure 28 (dashed rectangle in FIG. 1) for dilating an anatomical stricture. The variable dilation structure 28 with the predicted variable characteristic curve in FIG. 7, has a first linear diameter and pressure characteristic curve (solid line in Region A) defined by the Young's modulus of the inner balloon 12 and a second linear diameter and pressure characteristic curve (solid line in Region B) defined by the combined modulus of elasticity of the inner and the outer balloon 20.

In use, the assembly 10 allows a physician for example, to dilate an anatomical stricture with the use of the inner balloon 12 characteristic curve 32 alone, or the combination of the characteristic 32 with the outer balloon 20 characteristic curve 34 for a slightly larger diameter with a smaller incremental increase in pressure, without the need of withdrawing a narrow first balloon in a mono-layer balloon assembly and reinserting a wider second balloon, with all the inherent risks associated with reinserting a second balloon.

More particularly, the inner balloon 12 is more elastic and has the first characteristics 32 in FIG. 7, and the outer balloon 20 is less elastic. The combination of the inner and outer balloon 12 and 20 in dilation structure 28 advantageously gives a physician increased flexibility, by allowing him or her to increase the pressure in the desired working pressure range in FIG. 7, with a smaller increase in diameter of structure 28, for more precise dilating of an anatomical stricture with minimal chances of bursting.

For example, mono-layer balloon assemblies are known which have distention properties which are not variable and which behave similar to those in first characteristic curve 32 alone (solid and dashed line in FIG. 7) or second characteristic curve 34 alone, along their entire range in FIG. 7. In such mono-layer assemblies, it is possible to obtain significant dimensional variability only with an undesirable increase in size beyond the desired working pressure range, for example, the dashed line in FIG. 7. In contrast, the assembly 10 provides a clinician the opportunity to increase the pressure in the desired working pressure range without a significant diameter increase, while working in a safe working pressure range in FIG. 7. Advantageously, the assembly 10 provides a clinician with the ability to vary the inflated structure 28 diameter within a narrow-safe pressure range, and further allows a pressure increase with less size increase, than is provided by a conventional mono-layer balloon, resulting in improved substantially uniform radial pressure circumferentially about, along the length and diameter of the dilation structure 28 in proximity to the stricture being dilated. Further, the assembly 10 provides the benefit of eliminating the need to change to a second catheter with a larger balloon diameter when a larger dilating diameter is required in mono-layer assemblies, for example.

A further advantage of assembly 10, is that the structure 28 includes the outer balloon 20 enclosing the inner balloon 12, thereby minimizing the possibility of rupture of structure 28. If the inner balloon 12 should rupture, as can happen during inflation, the assembly 10 has a reduced potential for vessel damage and minimal chances of loosing a piece of the ruptured balloon in the bloodstream, because such pieces will be collected in the outer balloon 20. The outer balloon 20 and the inner balloon 12 reinforce the variable dilation structure 28 so as to minimize the possibility of rupture of balloons 12 and 20 individually, and also provides a more durable and resilient structure 28 which can withstand greater inflation pressures, and provide an improved degree of protection when expanded, inserted or removed, or when deploying a stent, which many times in a single balloon assembly has a tendency to puncture or burst.

The assembly 10 can be used for many types of dilation products, such as angioplasty, valvuloplasty, urethroplasty, salpingoplasty, and the like. The assembly 10 can be attached to an over the wire, fixed wire, hybrid over the wire or rapid exchange monorail type dilation system. The assembly 10 is particularly suited for dilating blood vessels within an area of stenosis.

The assembly 10 can also be used to deploy a stent in a body cavity or blood vessel (not shown in the drawings). The stent is received around the assembly 10 structure 28, and the entire dilating structure 28 and the stent is received within a body cavity. When the assembly 10 is used in conjunction with a stent, the elasticity of the balloons 12 and 20 exert radially outwardly pressure to and against a stent (not shown in the FIGS.), to expand the stent as desired against an appropriate body cavity. After the stent has been deployed, the dilating structure 28 is deflated and removed.

In one embodiment, the inner balloon 12 and the outer balloon 20 are tubular, annular, flexible and expandable and comprise a polymeric material.

In one preferred embodiment, the inner and outer balloons 12 and 20 comprise at least one polymeric material selected from the group consisting of polyolefins, copolymers of polyolefins, polyamides, polyvinyl chloride, polyethylene terephthalate, and combinations and permutations thereof, more preferably a polyamide such as nylon because of its desirable properties, such as elasticity, durability, formability, manufacturability, etc. In one preferred embodiment, the inner and outer balloons 12 and 20 comprise a polyamide such as 70D nylon and 75D nylon, respectively, for desirable properties.

In one embodiment, the balloon assembly 10 further includes a hub 36 having a first member 38 with a port 40 and an annular and tubular intermediate section 42 for inflating the inner balloon 12 until it reaches the outer balloon 20, and thereafter both balloons 12 and 20. The hub 36 is attached to and circumferentially around a proximal portion of the intermediate section 42, and the intermediate section 42 at the other end is attached to and circumferentially within a portion of the proximal portions 16 and 24 of the balloons 12 and 20 defining the dilation structure 28. The assembly 10 further includes an inflating device for inflating balloons 12 and 20, connected to member 38 (not shown in the drawings).

Referring to FIG. 5, the dilating structure 28 further includes the intermediate portions 18 and 26 of the inner and outer balloons 12 and 20 forming a first inclined section 46, a middle section 48 and a second inclined section 50. The first inclined section 46 is adjacent to the proximal portions 16 and 24 of the balloons 12 and 20, respectively, and the second inclined section 50 is adjacent to the distal portions 14 and 22 of the balloons 12 and 20, respectively. In one embodiment, the first and second inclined sections 46 and 50 extend outwardly at an angle ranging from about 5° to about 85° when dilated, with respect to an axial or elongate axis extending through the center of the assembly 10 in FIG. 5, and preferably ranging from about 15° to 60°, and most preferably about 45° for a smooth and gradual increase and decrease in diameter for improved durability and flexibility.

In one embodiment, the balloon assembly 10 includes a catheter 52 positioned and enclosed in the inner balloon 12 in alignment with the elongate axis for facilitating the insertion of the dilation structure 28 in a body cavity.

The balloon assembly 10 further includes a path 56 (dashed line) from the hub 36 port 40 to the proximal portion 16 of the inner balloon 12 for inflating the balloons 12 and 20. The path 56 provides a means for delivery of dilatation fluid, to structure 28. In one embodiment, the path 56 also receives the catheter 52 partially therealong.

The first modulus of elasticity of the inner balloon 12 the first Young's modulus of the inner balloon 12 can range widely. In one embodiment the rate of radial expansion ranges from about 2% per bar of internal balloon pressure to about 5% per bar of internal balloon pressure and typically is about 3.5% per bar of internal balloon pressure similarly, the second Young's modulus of the outer balloon 20 can range widely. Preferably it causes the combined rate of radial expansion to range from about 0.5% per bar of internal balloon pressure to about 2% per bar of internal balloon pressure, and typically is about 1% per bar of internal balloon pressure.

When balloon assembly 10 is fully inflated in the B Region in FIG. 7, the intermediate portions 18 and 26 of the balloons 12 and 20 in FIG. 5, are substantially adjacent and have a substantially similar dilation diameter therealong, with the diameter of the inner balloon 12 being slightly smaller than that of the outer balloon 20, for providing a substantially uniform and durable circumferential and outward radial pressure to the stricture being dilated.

The length of the dilation structure 28 can range widely depending on the intended application. In one embodiment, the length ranges from about 50 mm to about 10 mm, preferably about 30 mm to about 10 mm, and typically about 20 mm in length for angioplasty dilation products. Similarly, the diameter of the structure 28 can range widely depending on the intended application, preferably the diameter ranges from about 30 mm to about 1 mm, and more preferably from about 1 mm to about 5 mm in diameter when used as an angioplasty dilation product.

The balloons 12 and 20 each have wall thicknesses that can vary widely depending on the material utilized. In one embodiment, each balloon 12 and 20 has a wall thickness of about 2 mils or less, preferably about 1 mil or less when utilizing a polymeric material. One preferred material is a polyamide, for elasticity, durability, strength, and minimal volume and surface area for ease of insertion and withdrawal into and out of a body cavity.

In use, a physician utilizing dilation structure 28 performs the following procedure. First, a physician inserts structure 28 about the stricture to be dilated, such as in an area of stenosis. Next, he or she dilates dilation structure 28 in the stricture. Initially the inner balloon 12 diameter grows or increases independently until it reaches or touches the walls of the outer balloon 20 in FIGS. 5 and 6 (see the characteristic curve 32 in FIG. 7). Thereafter, as the pressure is further increased, the diameter of the dilation structure 28 increases more slowly than in characteristics 34, which is dependant upon the combined modulus of elasticity of the inner and outer balloon 20. The dilation step can include two stages, including following the solid line in Region A alone and thereafter, if needed, following the solid line in Region B. As pressure is increased, the dilation structure 28 diameter increases linearly and fairly rapidly as indicated in first characteristic curve 32. When Region B is reached, the inner balloon 12 reaches the outer balloon 20, as shown in FIG. 6, and the diameter increases more slowly but still linearly, as indicated in the second characteristic curve 34 (solid line). The balloons 12 and 20 improve resistance to rupture and provide a smooth circumferential surface and radial pressure along the middle section 48 of the dilation structure 28 about the stricture being dilated. Thereafter, the apparatus 10 is deflated and removed.

Although only one embodiment of this invention has been shown and described, it is to be understood that modifications and substitutions, as well as rearrangements and combinations of the disclosed embodiment can be made by those skilled in the art without departing from the teachings of this invention. Accordingly, the scope of the invention is only to be limited as necessitated by the accompanying claims.

I claim:

1. A variable distention angioplasty balloon assembly, for insertion into a blood vessel, comprising:

an inner elongated, inflatable balloon having a distal portion, a proximal portion and an intermediate portion therebetween and defining therein a first chamber, said inner balloon having a first Young's modulus;

an outer elongated, inflatable balloon having a distal portion, a proximal portion and an intermediate portion therebetween positioned around said inner balloon and defining between the balloons a second chamber, said outer balloon having a second Young's modulus, said inner balloon being substantially enclosed by said outer balloon, and said first Young's modulus of the inner balloon is less than the second Young's modulus of the outer balloon; and said first chamber of said inner balloon and said second chamber of said outer balloon define a variable dilation structure for dilating an anatomical stricture, said dilation structure with variable characteristics having a first diameter and pressure characteristic curve defined by a first rate of radial expansion dependent upon the Young's modulus of said inner balloon and a second diameter and pressure characteristic curve defined by a second rate of radial expansion dependent upon the combined Young's modulus of said inner balloon and said outer balloon.

2. The assembly of claim 1, wherein said inner and outer balloons are tubular, annular, flexible and expandable.

3. The assembly of claim 1, wherein said inner and outer balloons comprise a polymeric material.

4. The assembly of claim 1, wherein said inner and outer balloons comprise at least one polymeric material selected from the group consisting of polyolefins, copolymers of polyolefins, polyamides, polyvinyl chloride and polyethylene terephthalate.

5. The assembly of claim 1, further comprising a catheter aligned longitudinally in the inner balloon.

6. The assembly of claim 1, wherein said first rate of radial expansion of said inner balloon ranges from about 1% per atmosphere of internal balloon pressure to about 5% per atmosphere of internal balloon pressure.

7. The assembly of claim 1, wherein said second rate of radial expansion of said inner and outer balloons range from about 5% per atmosphere of internal balloon pressure to about 2% per atmosphere of internal balloon pressure.

8. The assembly of claim 1, further comprising a molded hub section having a port for inflating the balloons, and an intermediate section, the intermediate section is attached to a portion of the proximal portions of the inner and outer balloons at one end and attached to the hub at the other.

9. The assembly of claim 1, further comprising a molded hub section including a first member having a port including an intermediate tubular section extending and attached to and circumferentially within the proximal portions of said inner and outer balloons.

10. The assembly of claim 1, wherein said variable dilation structure includes said intermediate portions of the inner and the outer balloons being substantially adjacent therealong during dilation thereof.

11. The assembly of claim 1, wherein said variable dilation structure includes a length comprising the intermediate portions of the inner and the outer balloons of about 50 mm or less and a diameter of about 5 mm or less.

12. The assembly of claim 1, wherein said dilation structure includes a first inclined section, a middle section and a second inclined section, said first inclined section being located adjacent to said proximal portion of said inner and outer balloons and said second inclined section being located adjacent to said distal portions of said inner and outer balloons.

13. The assembly of claim 12, wherein said first and said second inclined sections extend outwardly at an angle ranging from about 5° to about 85° with respect to an elongate axis extending through the assembly.

14. The assembly of claim 1, further comprising a catheter therealong positioned in the inner balloon.

15. The assembly of claim 1, wherein the first balloon and the second balloon are impermeate.

16. The assembly of claim 1, further comprising means for inflating said inner and outer balloons.

17. The assembly of claim 1, wherein the first balloon and second balloon each have a substantially uniform wall thickness of about 2 mils or less.

* * * * *